United States Patent [19]
Linxweiler

[11] Patent Number: 6,004,769
[45] Date of Patent: Dec. 21, 1999

[54] COMPOSITIONS AND PROCEDURES FOR THE DETERMINATION OF HYDROLYTIC ENZYMES

[75] Inventor: Winfried Linxweiler, Gross-Umstadt, Germany

[73] Assignee: Merck Patent Gesellschaft, Darmstadt, Germany

[21] Appl. No.: 08/989,774

[22] Filed: Dec. 12, 1997

[30] Foreign Application Priority Data

Dec. 13, 1996 [DE] Germany .................. 196 51 886

[51] Int. Cl.⁶ .................. C12Q 1/34; C12N 9/14
[52] U.S. Cl. .................. 435/18; 435/195
[58] Field of Search .................. 435/7.37, 7.91, 435/18, 19, 20, 21, 22, 23, 24, 195, 196, 198, 200, 212, 213, 219, 805, 810

[56] References Cited

U.S. PATENT DOCUMENTS

| | | | |
|---|---|---|---|
| 3,699,005 | 10/1972 | Foster et al. | 435/21 |
| 4,278,763 | 7/1981 | Berger et al. | 435/23 |
| 4,376,197 | 3/1983 | Wallenfels | 536/17.4 |
| 4,801,535 | 1/1989 | Babler et al. | 435/16 |
| 4,892,817 | 1/1990 | Pawlak | 435/21 |
| 4,952,495 | 8/1990 | Belly et al. | 435/18 |
| 5,051,358 | 9/1991 | Witt | 435/19 |
| 5,200,317 | 4/1993 | Georgevich | 435/7.4 |
| 5,202,233 | 4/1993 | Herrmann et al. | 435/7.4 |
| 5,443,986 | 8/1995 | Haughland | 435/4 |

FOREIGN PATENT DOCUMENTS

| | | |
|---|---|---|
| 0 237 394 | 9/1987 | European Pat. Off. . |
| 0 290 217 | 11/1988 | European Pat. Off. . |
| 0 381 173 | 8/1990 | European Pat. Off. . |
| 1128371 | 9/1968 | United Kingdom . |
| 1128371 | 11/1968 | United Kingdom . |

OTHER PUBLICATIONS

Burstone, J. National Cancer Institute, vol. 24, 1199–1217 (1960).
Chemical Abstracts; Shikenjyochoh C; 89–098039/13; JP 01047–399–A; Aug. 14, 1987.
Chemical Abstracts; Konishiroku Photo KK, 89–125946/17; JP 01071–499–A; Sep. 10, 1987.

*Primary Examiner*—Jean C. Witz
*Assistant Examiner*—Susan Hanley
*Attorney, Agent, or Firm*—Millen, White, Zelano & Branigan

[57] ABSTRACT

The invention relates to compositions and procedures for the determination of hydrolytic enzymes in liquid samples with the aid of indoxyl compounds and oxidizing agents. The procedure is characterized in that the absorbent carrier impregnated with an indoxyl compound is wetted with the sample solution, immersed in the solution comprising the oxidizing agent, incubated and analysed by reflectometry.

5 Claims, 4 Drawing Sheets

COMPOSITIONS AND PROCEDURES FOR THE DETERMINATION OF HYDROLYTIC ENZYMES

The invention relates to compositions and procedures for the determination of hydrolytic enzymes in liquid samples, e.g. in foodstuffs and biological solutions, with the aid of solid reagent carriers and quantitative determination by means of reflectometry.

Hydrolytic enzymes in foodstuffs originate either from the foodstuff itself or from microorganisms which contaminate the foodstuffs. These enzymes are often the reason for foodstuff decay, particularly if the enzymes are not completely inactivated by the methods of sterilizing the foodstuffs. Such hydrolases are, for example, lipases, ali- and arylesterases, phosphatases, sulphatases, glucuronidases, glucosidases, amylases and proteinases. Hydrolytic enzymes in biological solutions such as blood, plasma, serum, urine, etc. are, for example, lipase, amylase, proteinases, cholinesterases and phosphatases. A change in their concentration can indicate disease states or certain physiological states. The rapid and sensitive determination of the concentration is important for the diagnosis of these states.

The determination of hydrolytic enzymes with the aid of absorbent carriers which contain both an indoxyl ester and an oxidizing agent, together on a carrier are disclosed in GB 1128371 and EP 12957. A test paper for the detection of esterases in animal and vegetable tissues and microorganisms, which contains indoxyl acetate, is known from Nahrung 9, 445 (1965). Atmospheric oxygen serves as an oxidizing agent. The period of time up to the occurrence of a colour reaction allows an estimation of the esterase concentration.

The disadvantage of the known procedures lies in the restricted sensitivity, in particular in samples with high fat, protein, salt and foreign substance content. Additionally, the enzyme activity can only be estimated in the case of the procedure to be evaluated visually.

The invention is based on the object of making available a composition and procedure for the determination of hydrolytic enzymes using which substantially higher sensitivities can be achieved in comparison with the prior art and which makes possible quantitative determinations.

Surprisingly, it has been found that by means of the presence of the oxidizing agent in a separate solution and by means of the immersion of the absorbent carrier containing the indoxyl compound in this solution a sensitivity which is higher than was previously possible by the factor 3–12 is achieved. A further advantage is the greater keeping ability which is associated with the separation of the reaction components, and also the low amount of substrate which is needed.

The invention relates to a composition for the determination of hydrolytic enzymes in liquid samples with the aid of indoxyl compounds and oxidizing agents, which is characterized in that the indoxyl compounds are present on an absorbent carrier and the oxidizing agents in solution.

The invention further relates to a procedure for the determination of hydrolytic enzymes in liquid samples, which is characterized in that the absorbent carrier impregnated with an indoxyl compound is wetted with the sample solution, immersed in the solution containing the oxidizing agent, incubated and analysed by reflectometry.

The indoxyl compounds present on the absorbent carrier are specific enzyme substrates for the hydrolytic enzymes. Suitable indoxyl compounds are, for example, indoxyl esters having 2–20 C atoms in the ester moiety such as indoxyl acetate, butyrate, caprylate, palmitate, indoxyl glucuronide, galactoside, -maltotriose, phosphate, sulphate, preferably halogen-substituted indoxyl esters such as 5-bromoindoxyl, 6-chloroindoxyl, 5-bromo-6-choloroindoxyl and 5-bromo-4-chloroindoxyl esters, preferably 5-bromo-4-chloro-3-indoxyl caprylate, 5-bromo-4-chloroindoxyl phosphate and indoxyl acetate. For other examples of indoxyl compounds, see the references cited in the third paragraph of the specification, and, e.g., Chemical Abstracts 89-125946/17 and 89-098039/13. The nature of the indoxyl compounds is not critical; any agent compatible with the disclosed reaction and determination may be used.

Absorbent carriers which can be used are all those which are customarily used for such tests. The use of filter paper is most widespread, but other absorbent cellulose or plastic products can also be employed. The absorbent carriers, preferably filter paper, are impregnated in a known manner with impregnating solutions which contain the indoxyl compounds. The impregnated and dried papers can be processed to give square or rectangular zones which for their part can be stuck onto or sealed onto plastic films, paper or metal strips in a known manner.

The absorbent carriers can also be applied to a plastic tape in strip form before impregnation and cut into manageable strips perpendicularly to the direction of the strip after impregnation.

The impregnating solution contains approximately 0.005-2 g, preferably 0.05 g, of the corresponding indoxyl compound in 100 ml of an organic solvent, e.g. in ethanol, methanol or acetone. If appropriate, the impregnating solution can additionally contain water, buffer substances, complexing agents and catalysts. The test paper is advantageously stored at 4–80° C. protected from light and moisture.

The oxidizing agents present in solution are tetrazolium salts such as Nitro Blue Tetrazolium Chloride, Tetranitro Blue Tetrazolium Chloride (TNBT), dimethylthiazolyl-diphenyltetrazolium bromide (MTT), Tetrazolium Blue Chloride, triphenyltetrazolium chloride, iodophenylnitro-phenylphenyltetrazolium chloride (INT), neotetrazolium chloride, phenylaminocarboxyl-tetrazolium-bismethoxynitrobenzenesulphonic acid sodium salt (XTT), preferably Nitro Blue Tetrazolium Chloride (NBT) . The tetrazolium salts are dissolved in a suitable solvent, preferably ethanol, and adjusted to a concentration of 0.02–10 mg/ml, preferably 1 mg/ml, using water. This solution can also contain further stabilizing additives, e.g. detergents. For other examples of oxidizing agents, see the references cited in the third paragraph of the specification, and, e.g., Chemical Abstracts 89-125946/17 and 89-098039/13. The nature of the oxidizing agents is not critical; any agent compatible with the disclosed reaction and determination may be used.

The ratio of indoxyl compound to oxidizing agent is not critical. A weight ratio of 10:2 to 1:20 is typical, preferably about 1:2.

To carry out the enzyme determination, the sample is either employed directly, diluted with a buffer or extracted. The buffer substances should be able to maintain a pH range of 6–11, preferably a pH range of approximately 8. The buffer concentration to be employed depends on the pH of the sample solution. Suitable buffers are, for example, tris/HCl buffer, HEPES buffer, MOPS buffer, sodium hydroxide solution/tartrate buffer, sodium hydroxide solution/borate buffer, sodium carbonate/sodium hydrogencarbonate buffer, preferably tris/HCl buffer.

The absorbent carrier is immersed in the sample solution for approximately 2 seconds, vigorously shaken off or scraped off and immersed in the tetrazolium salt solution such that the reaction zone is completely wetted. The immersion time is between 1 and 60 minutes, preferably approximately 15 minutes. The carrier is then removed from the sample solution and vigorously shaken off, and the resulting colouration is analyzed using a reflectometer (340–700 nm) or with the aid of a colour comparison scale. Using the procedure according to the invention, a rapid, accurate and highly sensitive determination of hydrolytic enzymes, in particular of lipases, esterases, phosphatases and sulphatases, is possible.

BRIEF DESCRIPTION OF THE DRAWINGS

Various other features and attendant advantages of the present invention will be more fully appreciated as the same becomes better understood when considered in conjunction with the accompanying drawings, in which like reference characters designate the same or similar parts throughout the several views, and wherein.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German application No. 196 51 886.5, filed Dec. 13, 1996 is hereby incorporated by reference.

EXAMPLE 1

Determination of Lipase a) Preparation of the Test Paper

A filter paper (Scholler & Hosch 300A) is impregnated with a solution of 56 mg of 5-bromo-4-chloro-3-indoxyl caprylate in 112 ml of ethanol (96%) and dried after impregnation. The paper obtained is applied to a carrier material, e.g. polyester film, in a known manner.

b) Preparation of the oxidizing agent solution

The oxidizing agent solution contains 60 mg of Nitro Blue Tetrazolium Chloride, which is dissolved in 12.5 ml of ethanol (96%). This solution is added to 49.3 ml of water which contains 1.5 g of detergent (Tween 20).

c) Preparation of the Lipase Standard Solutions

Using lipoprotein lipase from Pseudomonas sp. by diluting with a buffer solution containing

| | |
|---|---|
| 500 mmol/l | of tris/HCl buffer, pH 8.0 |
| 4 mmol/l | of magnesium chloride |
| 2 mmol/l | of EDTA |
| 0.1 mmol/l | of bovine serum albumin and |
| 2% | Tween 20 | lipase standard solutions in the concentrations 10, 20, 60, 120, 200, 300, 450 and 600 µg/l are prepared.

d) Determination of the lipase

The test strip is immersed in the enzyme solution for approximately 2 seconds, shaken off- and immersed in approximately 1 ml of the oxidizing agent solution for 15 minutes. After this time, a blue colour which is measured in a reflectometer (576 nm) has developed:

| Conc. (µg/l) | 10 | 20 | 60 | 120 | 200 | 300 | 450 | 600 |
|---|---|---|---|---|---|---|---|---|
| Relative reflectance (%) | 71.4 | 68.4 | 60.8 | 53.9 | 48.7 | 43.3 | 38 | 32.2 |

Figure 1:
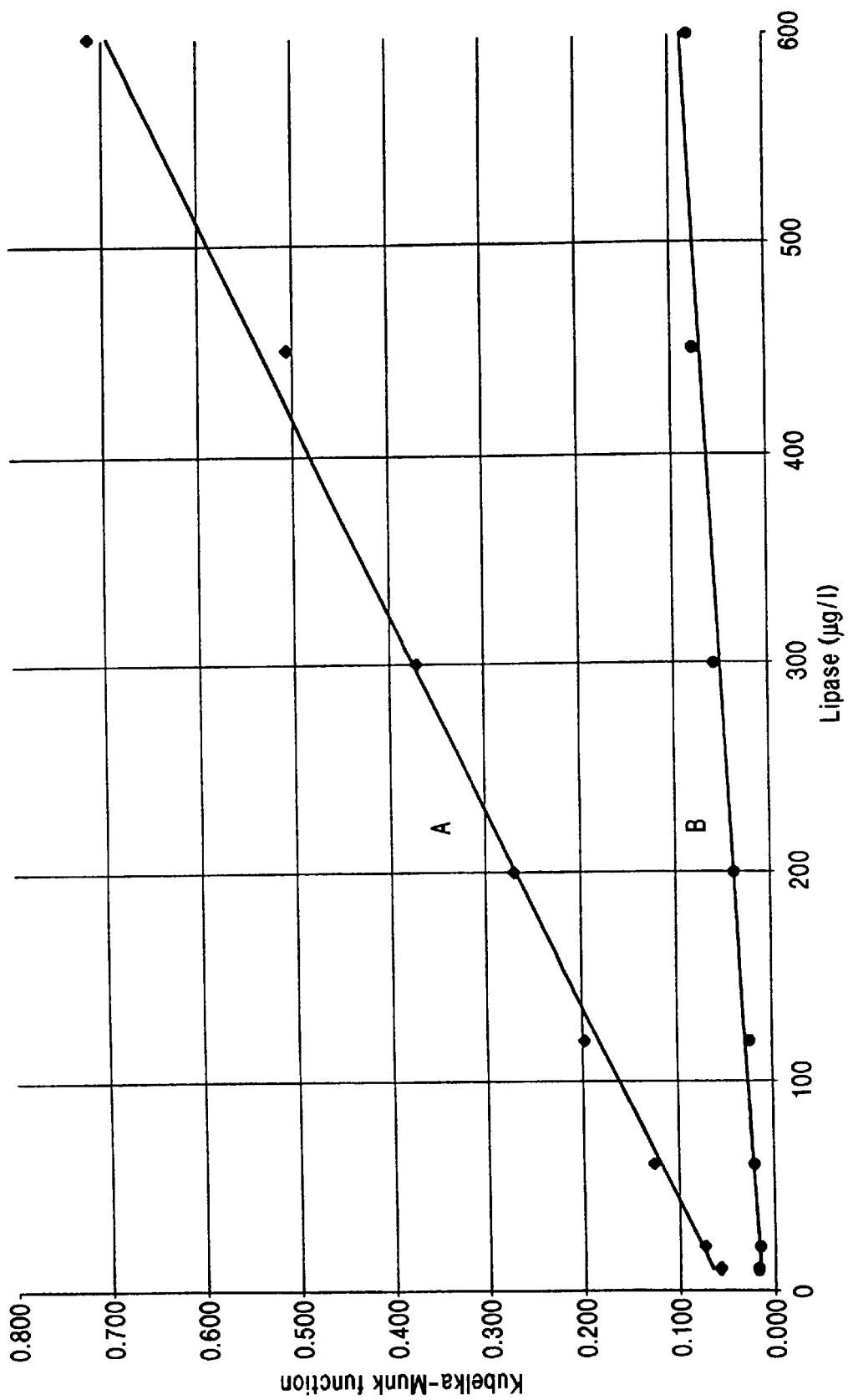
FIG. 1 is a graph of Lipase vs. Kubelka-Munck function.

These results are shown diagrammatically in FIG. 1A. The measured reflectance values were converted according to the procedure of Kubelka and Munk (Z. Tech. Physik 12, 593 (1931)) according to the equation $F=(1-R)^2/2R$ (Kubelka-Munk function) in order to obtain a linear relationship to the enzyme concentration. The straight line obtained corresponds to a linearized standard curve having a gradient of $y=0.0011x$.

e) Comparison Experiment

According to the prior art, both substrate and oxidizing agent are applied together to an absorbent carrier. A filter paper is impregnated with a solution of 56 mg of 5-bromo-4-chloro-3-indoxyl caprylate and 112 mg of Nitro Blue Tetrazolium Chloride in 112 ml of ethanol and dried. The test paper obtained is immersed for about 2 seconds in the standard solutions according to c), shaken off and incubated for 15 minutes lying flat, and analysed according to d):

| Conc. (µg/l) | 10 | 20 | 60 | 120 | 200 | 300 | 450 | 600 |
|---|---|---|---|---|---|---|---|---|
| Relative reflectance (%) | 86 | 80.9 | 79.2 | 75 | 77.1 | 73.5 | 67 | 56.4 |

The result is shown diagramatically in FIG. 1B with the result that the straight line has a gradient of $y=0.0001$, i.e. that the procedure according to the invention is more sensitive by the factor 11 than the procedure according to the prior art. Analogous results are obtained if 5-bromo-3-indoxyl caprylate, 6-chloro-3-indoxyl caprylate, 5-bromo-6-chloro-3-indoxyl caprylate or the corresponding palmitates or acetates are employed instead of 5-bromo-4-chloro-3-indoxyl caprylate.

EXAMPLE 2

Determination of Lipase in Milk

The determinations are carried out analogously to Example 1, the lipase standard solution being diluted with pasteurized whole milk (fat content 3.5%) instead of the buffer solution. The table below shows the results of the measurement using the reflectometer:

| Conc. (µg/l) | 10 | 20 | 60 | 120 | 200 | 300 | 450 | 600 | |
|---|---|---|---|---|---|---|---|---|---|
| Relative reflectance (%) | 75.1 | 69.7 | 63.8 | 54.1 | 43.7 | 38.8 | 36.1 | 31.8 | (A) |
| | 84.0 | 83.5 | 81.5 | 74.1 | 73.5 | 72.5 | 66.5 | 47.3 | (B) |

Figure 2:
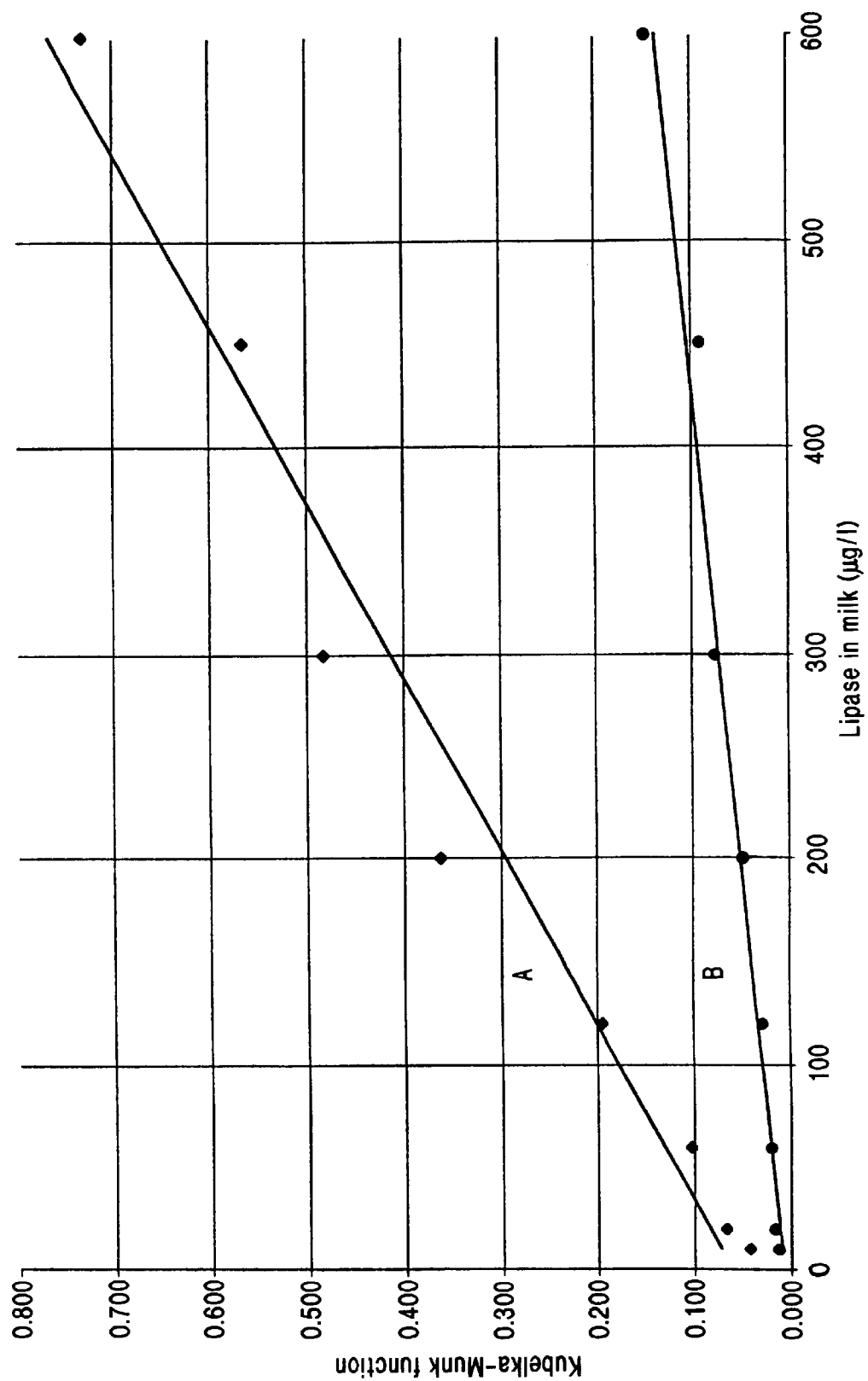
FIG. 2 is a graph of Lipase in milk versus Kubelka-Munck function.

The results are shown diagrammatically in FIG. 2, the straight line A representing the results according to the invention and the straight line B the results according to the prior art. From the gradients of the two straight lines ($y=0.0012x$ and $y=0.0002x$), it is evident that the procedure according to the invention is 6 times more sensitive than that according to the prior art.

EXAMPLE 3

Determination of Lipase in Serum

The determinations are carried out analogously to Example 1, the lipase standard solution containing 0, 10, 20, 50, 100, 200, 500 and 1000 µg/l of lipase being diluted with human serum which is heated to 65° C. for 10 minutes instead of the buffer solution. The result is presented in the table below. It is seen that 2 µg/l of lipase can also be safely detected.

| Lipase in serum (µg/l) | Test strip R (% reflectance) | Test strip Ro—R (% reflectance) | Wet-chemical test (U/l) |
|---|---|---|---|
| 0 | Ro = 59.9 | 0.0 | 0 |
| 1 | 59.7 | 0.2 | 0 |
| 2 | 57.3 | 2.4 | 0 |
| 5 | 56.3 | 3.4 | 0 |
| 10 | 53.6 | 6.1 | 0 |
| 20 | 48.9 | 10.8 | 0 |
| 50 | 39.2 | 20.5 | 4 |
| 100 | 30.2 | 20.5 | 67 |
| 200 | 21.8 | 37.9 | 156 |
| 500 | 13.4 | 46.3 | 305 |
| 1000 | 9.0 | 50.7 | 753 |

The results according to the invention (column 3) are compared with a commercially available photometric, witchemical lipase test (column 4). The activity was measured on a clinicochemical analyser. The result shows that a value other than zero is found only from 50 µg/l of lipase. The procedure according to the invention is thus approximately 25 times more sensitive than the commercially available lipase test.

Determination of Alkaline Phosphatase a) Preparation of the Test Paper

A filter paper (Scholler & Hosch 300A) is impregnated with a solution of 56 mg of 5-bromo-4-chloro-3-indoxyl phosphate in 112 ml of ethanol (96%) and dried after impregnation. The paper obtained is applied to a carrier material, e.g. polyester film, in a known manner.

b) Preparation of the Oxidizing Agent Solution

The oxidizing agent solution contains 60 mg of Nitro Blue Tetrazolium Chloride which is dissolved in 9.9 g of ethanol (96%). This solution is added to 49.3 ml of water which contains 2% detergent (Tween 20).

c) Preparation of the Alkaline Phosphatase Standard Solutions

Using alkaline phosphatase from calves' intestine, by diluting with a buffer solution comprising 1 mol/l of diethanolamine, pH 9.8 and 0.5 mmol/l of magnesium chloride standard solutions are prepared in the concentrations 0.1, 0.2, 0.5, 1, 2, 5 and 10 µm g/l.

d) Determination of the Alkaline Phosphatase

The test strip is immersed in the enzyme for approximately 2 seconds, shaken off and immersed in approximately 1 ml of the oxidizing agent solution for 15 minutes. After this time, a blue colour has developed which is measured in a reflectometer (576 nm):

| Conc. (µg/l) | 0 | 0.1 | 0.2 | 0.5 | 1 | 2 | 5 | 10 |
|---|---|---|---|---|---|---|---|---|
| Relative reflectance (%) | 74.5 | 73.89 | 73.4 | 71.2 | 67 | 62.4 | 48.5 | 34.4 | e) Comparison experiment

According to the prior art, both substrate and oxidizing agent are applied together to an absorbent carrier. A filter paper is impregnated with a solution of 56 mg of 5-bromo-4-chloro-3-indoxyl phosphate and 112 mg of Nitro Blue Tetrazolium Chloride in 112 ml of ethanol and 10 dried. The test paper obtained is immersed in the standard solutions according to c), shaken off and incubated at room temperature for 15 minutes lying flat. After this, a blue colour has developed which is measured in the reflectometer.

| Conc. (µg/l) | 0 | 0.1 | 0.2 | 0.5 | 1 | 2 | 5 | 10 |
|---|---|---|---|---|---|---|---|---|
| Relative reflectance (%) | 76.8 | 75.7 | 76.1 | 74.5 | 73.1 | 71.2 | 61.5 | 54.5 |

Figure 3:
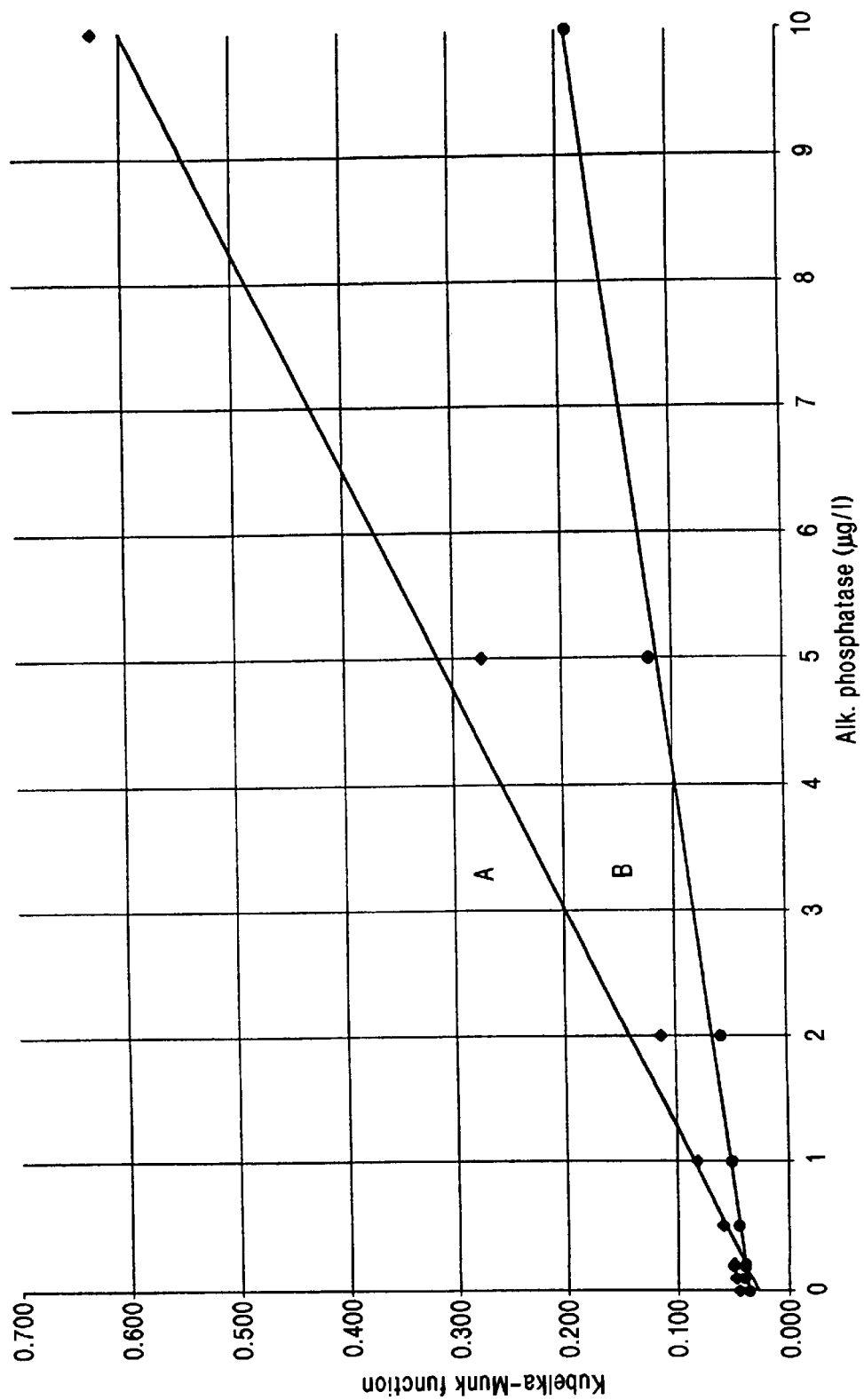
FIG. 3 is a graph of Alkaline phosphatase versus Kubelka-Munck function.

The results from d) and e) are shown diagrammatically in FIG. 3. In this figure, the reflectance values were converted according to the procedure of Kubelka-Munk according to the equation $F=(1-R)^2/2R$ and a linear relationship to the enzyme content was thus obtained. The straight line A represents the results according to the invention and the straight line B the results according to the prior art. From the gradients of the two straight lines ($y=0.0574x$ and $y=0.0157x$) it is evident that the procedure according to the invention is 3.6 times more sensitive than the procedure according to the prior art.

EXAMPLE 5

Determination of esterases

Analogously to Example 4, a test paper is prepared which is impregnated with a solution of 56 mg of N-methylindoxyl acetate in 112 ml of ethanol (96%). The oxidizing agent solution corresponds to that in example 4d). The esterase standard solutions in the concentrations 1, 2, 5, 10, 20, 50 and 100 µg/l of esterase from pigs' liver are prepared by diluting with a buffer solution comprising 20 mmol/l of tris/HCl buffer, pH 7.6

4 mmol/l of magnesium chloride 2 mmol/l of EDTA and 0.1 mg/ml of bovine serum albumin.

The test paper is immersed in the enzyme solution for approximately 2 seconds, shaken off and immersed in approximately 1 ml of the reaction solution for 15 minutes. After this time a blue colouration has developed which is measured in a reflectometer (576 nm).

| Conc. (µg/l) | 0 | 1 | 2 | 5 | 10 | 20 | 50 | 100 |
|---|---|---|---|---|---|---|---|---|
| Relative reflectance (%) | 78.8 | 75.5 | 72.1 | 71.8 | 67.4 | 59.6 | 44.1 | 32.3 |

For comparison, a test paper was prepared which is impregnated with a solution of 56 mg of N-methylindoxyl acetate and 112 mg of Nitro Blue Tetrazolium Chloride in 112 ml of ethanol, with the following result:

| Conc. (µg/l) | 0 | 1 | 2 | 5 | 10 | 20 | 50 | 100 |
|---|---|---|---|---|---|---|---|---|
| Relative reflectance (%) | 77.1 | 73.8 | 77 | 75.5 | 74.1 | 71.0 | 65.1 | 57.9 |

Figure 4:
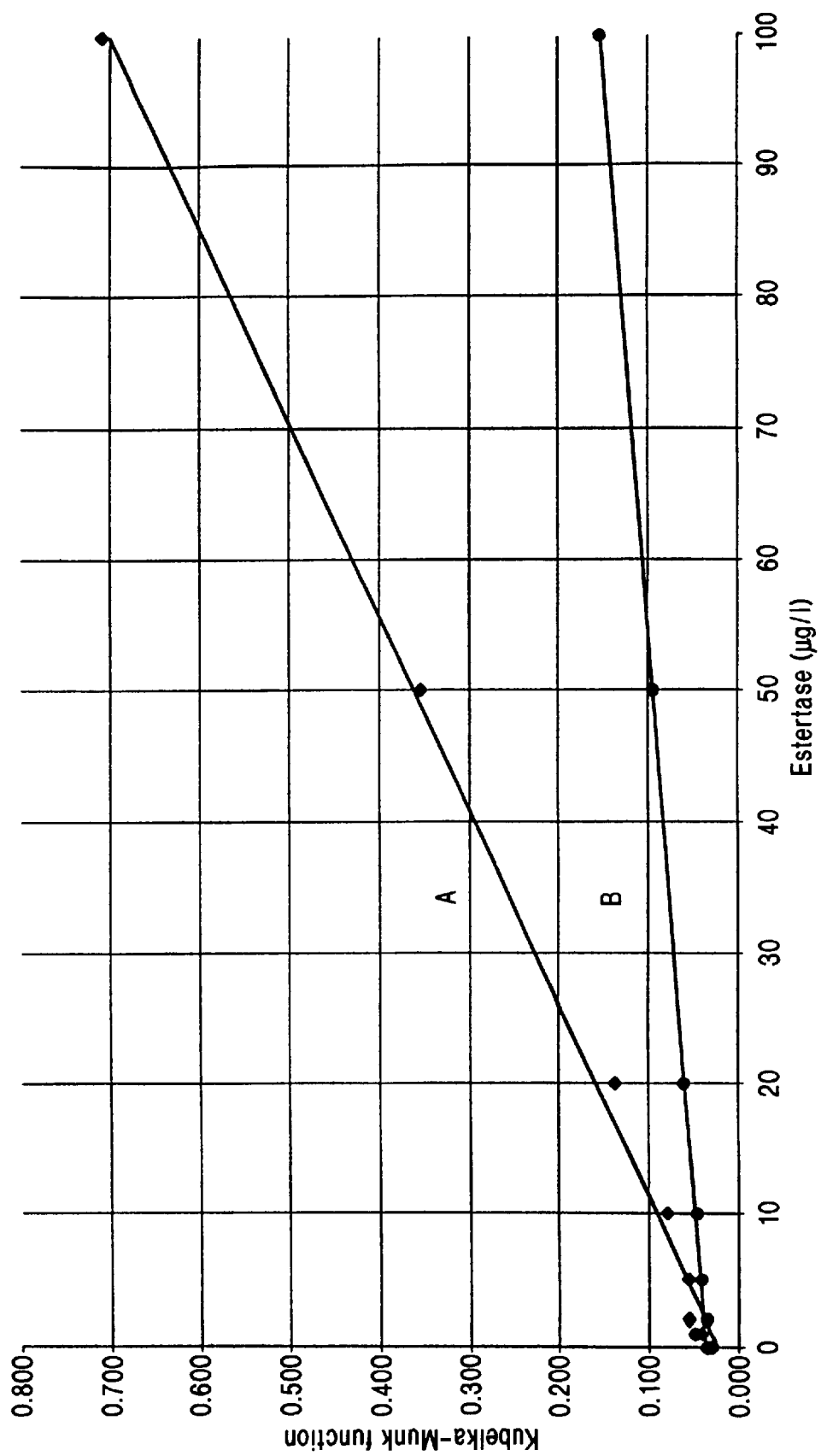
FIG. 4 is a graph of Esterase vs. Kubelka-Munck function.

The results from both experiments are shown diagrammatically in FIG. 4. The straight line according to the procedure according to the invention (A) has a gradient of $y=0.0068x$, that of the comparison experiment has a gradient of $y=0.0012x$. This means that the procedure according to the invention is more sensitive by the factor 5.7 than the procedure according to the prior art.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A procedure for the determination of hydrolytic enzymes in a first solution containing a test sample suspected of containing said hydrolytic enzymes, comprising
   (a) wetting an absorbent carrier with said first solution, wherein said carrier is impregnated with a compound having an indoxyl moiety such that said compound is a substrate for said hydrolytic enzymes;
   (b) immersing and incubating said wetted carrier in a second solution comprising an oxidizing agent;
   (c) removing said carrier from said second solution; and
   (d) detecting a color change on said carrier which indicates hydrolase activity by reflectometly or by color comparison.

2. The procedure of claim 1, wherein said compound is indoxyl acetate, indoxyl butyrate, indoxyl caprylate, indoxyl glucuronide, indoxyl galactoside, indoxyl maltotriose, indoxyl phosphate, indoxyl palmitate or indoxyl sulfate.

3. The procedure of claim 1, wherein the compound is a halogen-substituted indoxyl ester.

4. The procedure of claim 1, wherein the oxidizing agent is a tetrazolium compound.

5. The procedure of claim 1, wherein the weight ratio of said compound having said indoxyl moiety to said oxidizing agent in between 10:2 and 1:20.

* * * * *